(12) United States Patent
Kotlarchik et al.

(10) Patent No.: US 9,204,946 B2
(45) Date of Patent: Dec. 8, 2015

(54) LOCATING/GUIDANCE TIP ASSEMBLY FOR A LIQUID DROPLET SPRAY TEETH CLEANING SYSTEM

(75) Inventors: Garrett Kotlarchik, Seattle, WA (US); Joseph W. Grez, North Bend, WA (US); Craig Black, Bellevue, WA (US); Bart J. Massee, Haarlem (NL); Paul Bas, Eindhoven (NL); Peter Alexander Wachters, Helmond (NL); Katrina Rockey, Renton, WA (US); Wolter Benning, Seattle, WA (US); Jerry Wood, Fall City, WA (US); Paulus Cornelis Duineveld, Drachten (NL); Jozef Johannes Maria Janssen, Herten (NL); Petrus Henricus De Leeuw, Someren (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1350 days.

(21) Appl. No.: 12/673,824

(22) PCT Filed: Aug. 24, 2007

(86) PCT No.: PCT/IB2007/053402
§ 371 (c)(1),
(2), (4) Date: Sep. 1, 2011

(87) PCT Pub. No.: WO2008/001337
PCT Pub. Date: Jan. 3, 2008

(65) Prior Publication Data
US 2012/0160263 A1 Jun. 28, 2012

(51) Int. Cl.
*A61H 13/00* (2006.01)
*A61C 17/02* (2006.01)

(52) U.S. Cl.
CPC ......... *A61C 17/0202* (2013.01); *A61C 17/0217* (2013.01)

(58) Field of Classification Search
CPC ...... A61C 17/00; A61C 17/02; A61C 17/022; A61C 17/024; A61C 17/028; A61C 17/0202; A61C 1/0092; A61H 2201/105; A61M 35/003; A61M 35/0254; A61M 35/0258; A61M 35/0262; A61M 35/0275; A61M 35/0279
USPC ......... 601/154, 155, 159, 162, 165, 169, 160, 601/161; 433/80, 82, 88, 89
See application file for complete search history.

(56) References Cited

U.S. PATENT DOCUMENTS 1,121,214 A   12/1914  Welton
1,494,809 A * 5/1924  Sahr .............................. 433/89

(Continued)

FOREIGN PATENT DOCUMENTS

FR   1121214 A    7/1956
JP   9327332 A   12/1997

(Continued)

*Primary Examiner* — Justine Yu
*Assistant Examiner* — Michael Tsai

(57) ABSTRACT

The spray assembly for a droplet spray teeth cleaning system includes a guidance member at the end thereof. The spray assembly includes a nozzle through which a spray of liquid is directed to the teeth for cleaning. The guidance member is configured and mounted relative to the nozzle to provide a selected standoff distance between the nozzle and the teeth and includes a portion which is configured to fit in the interproximal space between adjacent teeth and gums, or against the frontal portions of the teeth, so that the user knows the location of the spray relative to the teeth.

9 Claims, 6 Drawing Sheets

(56) References Cited

U.S. PATENT DOCUMENTS

| | | | |
|---|---|---|---|
| 1,868,893 A * | 7/1932 | Gentle | 128/200.21 |
| 3,426,750 A * | 2/1969 | Clements | 601/160 |
| 3,496,933 A | 2/1970 | Lloyd | |
| 4,315,741 A | 2/1982 | Reich | |
| 4,386,911 A * | 6/1983 | Maloney et al. | 433/125 |
| 4,611,992 A | 9/1986 | Lokken | |
| 4,787,845 A | 11/1988 | Valentine | |
| 5,246,367 A * | 9/1993 | Ito et al. | 433/80 |
| 5,376,003 A * | 12/1994 | Rizkalla | 433/116 |
| 5,807,289 A * | 9/1998 | Camp | 601/160 |
| 5,890,898 A | 4/1999 | Wada et al. | |
| 6,245,032 B1 * | 6/2001 | Sauer et al. | 601/162 |
| 6,602,071 B1 | 8/2003 | Ellion et al. | |
| 2003/0215768 A1 * | 11/2003 | Aumuller et al. | 433/130 |
| 2005/0096573 A1 | 5/2005 | Liu | |
| 2005/0175960 A1 * | 8/2005 | Wiek et al. | 433/88 |

FOREIGN PATENT DOCUMENTS

| | | |
|---|---|---|
| WO | 2005007034 | 1/2005 |
| WO | 2005055863 A | 6/2005 |
| WO | 2005058186 A | 6/2005 |

\* cited by examiner

LOCATING/GUIDANCE TIP ASSEMBLY FOR A LIQUID DROPLET SPRAY TEETH CLEANING SYSTEM

This invention relates generally to liquid droplet spray teeth cleaning systems, and more particularly concerns a droplet spray portion of the teeth cleaning system which includes a guidance tip for properly locating the droplet spray relative to the teeth.

Droplet spray teeth cleaning systems are generally known, and various droplet spray systems are described in several patents and published patent publications. One such patent publication is WO200507034, which is owned by the assignee of the present invention, the contents of which are herein incorporated by reference. In that application, liquid (water) droplets are generated and then accelerated to a desired velocity by a stream of gas, such as air. In other systems, the liquid droplets are accelerated by other means, such as a swirl nozzle, using high pressure, to a desired velocity. The liquid droplets must have a particular size and velocity to produce an effective cleaning effect on the teeth.

Many of these devices are designed for home use, which requires the user himself/herself to properly locate the spray tip of the device relative to the teeth, so that the spray reaches the desired area of the teeth. This has proven to be a challenge, particularly locating the spray on the interproximal spaces between the teeth. It is difficult for the user to properly locate the spray tip because the spray itself cannot be directly felt by the user.

It is thus desirable that a droplet spray system include a locating/guidance tip assembly to position the droplet spray properly for effective cleaning, particularly over the interproximal area, but also over the front surface of the teeth as well. In addition, the distance between the origin of the spray and the teeth should be properly controlled for optimal efficiency as well as safety. The spray nozzle cannot be too close, which might cause damage to the gums and other tissues, but also cannot be too far away, as this results in a decrease in efficacy. The guidance tip should thus be arranged to provide both distance and location functions of the device relative to the teeth.

Furthermore, in some cases, it is important to be able to safely and effectively accommodate teeth braces with a droplet spray cleaning system.

Accordingly the present invention is a spray assembly for a droplet spray system for cleaning teeth, comprising: a spray assembly for use with a droplet spray teeth cleaning system which includes a spray nozzle through which a spray of liquid is directed to the teeth for cleaning thereof and a guidance member at a tip end thereof for locating the spray relative to the teeth, configured to provide a selected standoff distance between the teeth and the spray nozzle and to locate the spray assembly relative to the teeth.

Figure 1:
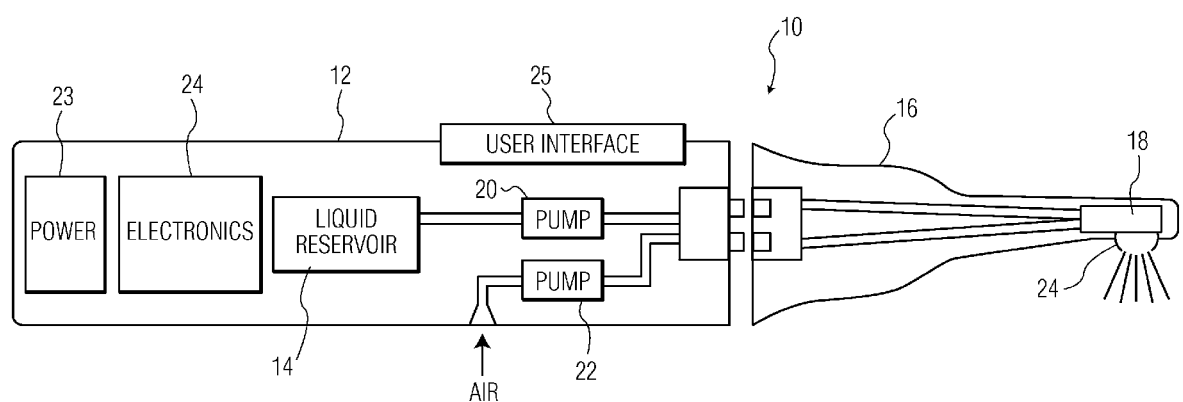
FIG. 1 is a simple schematic diagram showing in general a droplet spray teeth cleaning system, which includes a spray assembly portion.

FIG. 1 shows in general a droplet spray teeth cleaning system 10. A typical hand-held system for home use will include a body or handle portion 12 in which is located a source of liquid 14. In one arrangement, air and the liquid are moved to a head portion 16 of the system by pumps 20-22. The liquid and gas are directed to a spray assembly 18 in which the gas stream produces and accelerates liquid droplets to a desired velocity as they move out of a nozzle 24 at the end of the head portion to a desired location on the teeth.

In one example, the droplets have a size range of 10-15 mm and are accelerated to a velocity of approximately 30 meters per second. Other arrangements, however, with different size droplets and different velocities can be used, for instance, at velocities up to 70 meters per second. In the present embodiment, the head portion 16 is arranged to be replaceable relative to the handle portion, which includes sources of gas and liquid, the electronic control portion 24 and the power supply 23 for the system, as well as a user interface 25, with an on/off switch 30.

What is shown and described herein is a guidance tip/member which is located at the forward end of the head portion 16 for correctly positioning the spray nozzle 24 within the mouth relative to the teeth, in order to accomplish effective cleaning without damaging the tissue or gums of the user. It should be understood that the guidance member described and shown can be used with a variety of droplet spray cleaning systems.

Figure 2A:
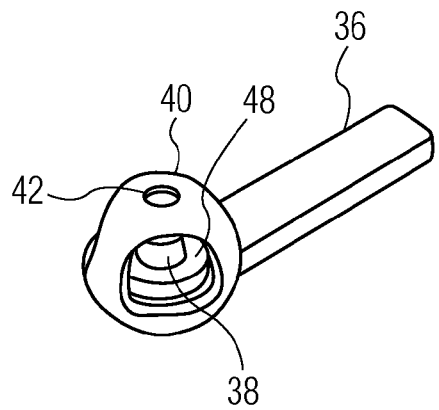
FIGS. 2A-2C are perspective views of several variations of one embodiment of the spray assembly system of the present invention, in particular a locating/guidance tip assembly.
Figure 2B:
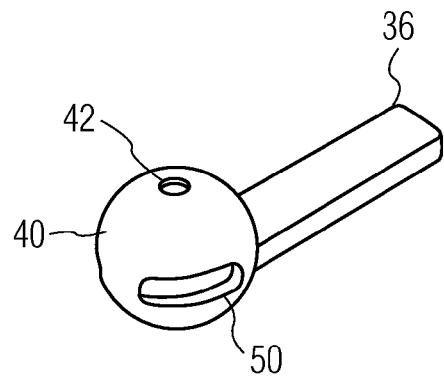
Figure 2C:
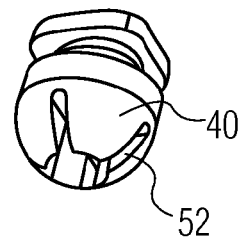

A first embodiment of a guidance member is shown in FIGS. 2A-2C. The head portion of the cleaning device includes a neck 36, which could be rigid or flexible, at the end of which is a spray nozzle 38, through which the accelerated liquid droplets are directed. In this embodiment, at the very end of neck 36, partially surrounding the spray nozzle, is a conical or approximately spherical element 40 which includes a spray opening 42, located a small distance, within the range of 1-15 mm, and more preferably 3-8 mm, from nozzle opening 38. The guidance member is made from a soft pliable material, such as rubber, which will not harm gums or other soft tissue.

Other openings in the conical/spherical member 40 are provided around the periphery thereof. These openings could be of various configurations, as shown in FIGS. 2A-2C, including spaced parabolic openings 48 in FIG. 2A, spaced horizontal slots 50 in FIG. 2B or spaced vertical slots 52 in FIG. 2C, which connect to spray opening 42. These openings are for the purpose of allowing venting of liquid, and optionally gas, during operation of the system, to prevent pooling of liquid around the nozzle.

The exterior surface of guidance member 40 is curved so as to fit readily between adjacent teeth and the gums, thus readily locating the interproximal area of the teeth for the user.

The diameter of the spray opening 42 is such that it is slightly larger than the desired footprint of the spray on the teeth. Further, the distance between the guidance member 40 and spray nozzle 38 provides a safe stand-off distance between the spray as it emerges from the nozzle and the teeth. In operation, the user will simply press the guidance member against the teeth, thereby guaranteeing a safe stand-off distance for all cleaning, as well as proper interproximal location when located between the teeth. The guidance member can be moved sideways to locate the spray accurately onto the front surface of the teeth as well.

Figure 3:
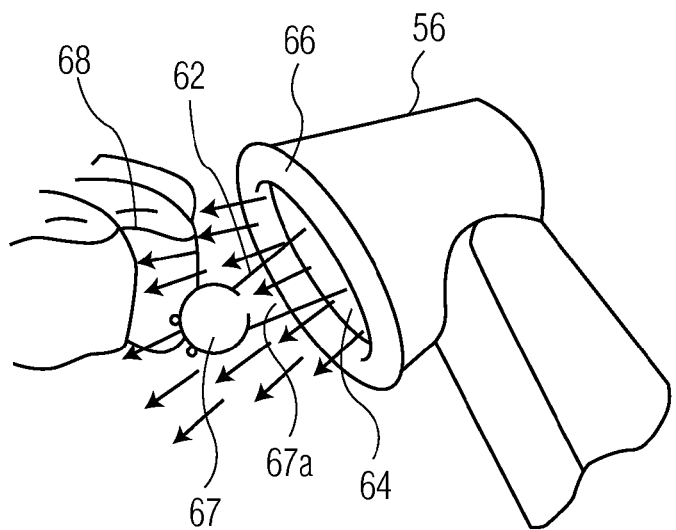
FIG. 3 is a perspective view of another embodiment of the locating tip assembly.

FIG. 3 shows another embodiment, in which a guidance member 56 includes a center elongated bumper member 62, surrounded by a spray nozzle 64, and boundaried by a ring member 66. The elongated bumper member 62 somewhat resembles a large toothpick. Typically, member 62 is a rubber or flexible member which will not damage gums or braces and has a certain mechanical cleaning effect in addition to its guidance and stand-off capabilities. Bumper member 62 extends beyond the ring member 66 a distance which provides a desired standoff distance for the spray. This is typically in the range of 1-15 mm, more preferably between 3-8 mm. The ring member 66 will typically be 8-25 mm in diameter.

The bumper member 62 can take various configurations, and will include a spherical portion 67 at the very end thereof, as shown in FIG. 3. In the embodiment, the spherical portion has a diameter of approximately 1-10 mm and preferably 1-2 mm. The elongated portion 67a is slightly conical in shape, with a diameter of its base of 2-10 mm, preferably 2 mm, and a diameter at the forward end, adjacent spherical portion 67, of 0.5-7 mm, preferably 0.5-1 mm. In this arrangement, the interproximal area 68 of the teeth is located quickly and accurately by the user, so that the user can know that the spray is located at the interproximal area. The device can also be moved sideways for reliable frontal surface cleaning of the teeth.

Figure 4A:
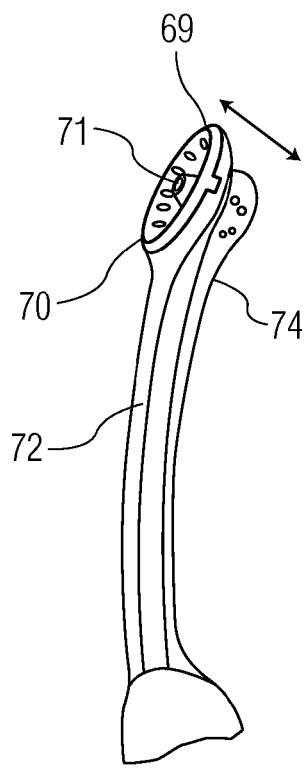
FIGS. 4A-4C are perspective views showing another embodiment of the locating tip assembly.
Figure 4B:
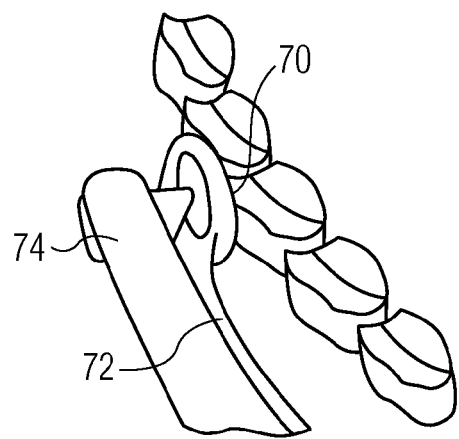
Figure 4C:
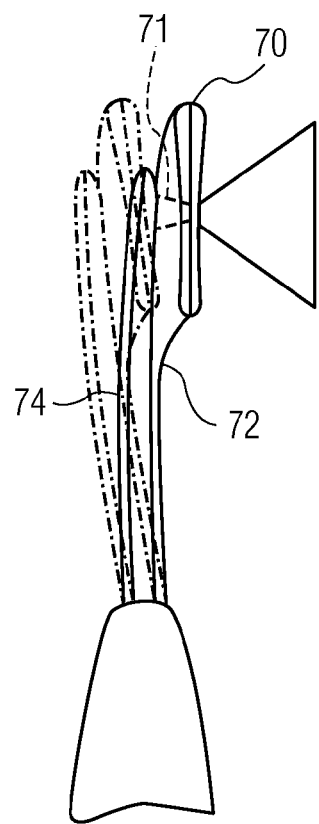

FIGS. 4A-4C show another embodiment of the spray assembly with a guidance member 69. In this arrangement, the head assembly includes a spray nozzle 71 which creates a spray directed to the teeth. The guidance member includes a flexible circular ring 70 surrounding the nozzle 71. In this arrangement, the spray from nozzle 71 is directed through the area enclosed by the circular ring but is not obstructed by it. Circular ring 70 is made from a flexible material, and is mounted on a spring arm 72 which is connected to a neck portion 74 of the head assembly of the system.

The advantage to this arrangement is that it provides a distance stand-off locator to provide safety for the user (gums and tissues) with good cleaning efficacy (the nozzle portion can be pushed into the interproximal areas of the teeth) and is useful with teeth with braces. The circular ring member 70 is hard enough to slide over the braces readily without being caught or snagged. Conventional toothbrush bristles could be used around the outside of ring 70 for additional cleaning effect. A conical/spherical structure, such as shown in FIGS. 2A-2C, can also be included to provide a reliable location of the interproximal regions. The arrangement of FIG. 4A-4C is easy to use, efficient and safe, and is particularly adapted for use with teeth with braces. The ring can also include openings to prevent pooling of liquid in the ring.

Figure 5A:
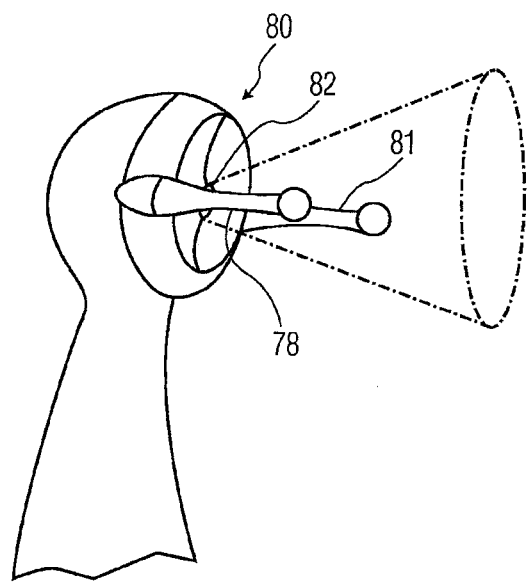
FIGS. 5A and 5B are perspective views of variations of another embodiment of the locating tip assembly.
Figure 5B:
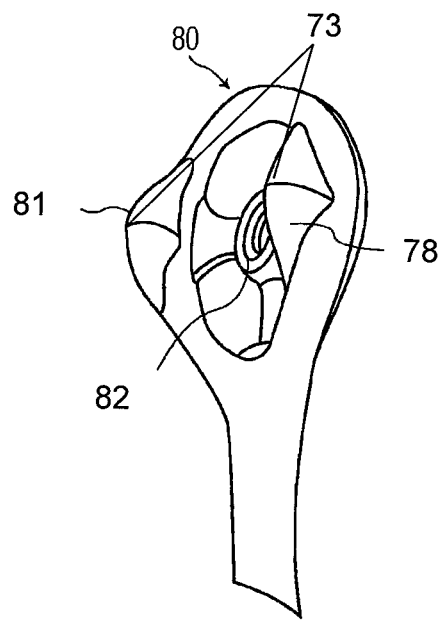
Figure 6:
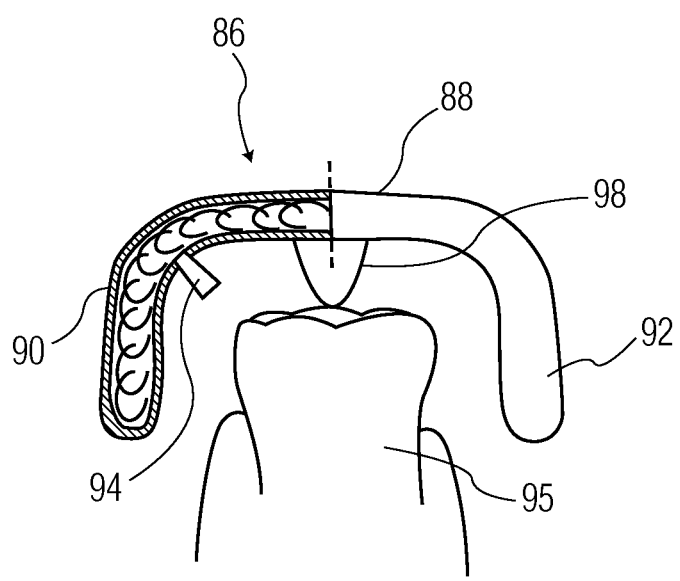
FIG. 6 is a cross-sectional view of another embodiment of the locating tip assembly.

FIGS. 5A-5B show a further embodiment in which a guidance member 80 includes two generally opposing elongated bumper members 78 and 81, which extend outwardly from both sides of a spray nozzle 82 located at the forward end of the spray head assembly. Bumper members 78 and 81 are made from material which is soft enough so that they don't harm the gums or tissues, but strong enough to give sensory feedback to the user as to location of the spray nozzle. This arrangement can also be used with multiple spray nozzles, some of which may cross each other.

The bumper members 78, 81 can take various configurations, as shown in FIGS. 5A and 5B. They can be elongated, like a toothpick (FIG. 5A) or more like a rib, with a wide base, tapering to a curved point 73, as shown in FIG. 5B. The bumper members are arranged so that they both can ride in the same interproximal area of the teeth, providing a very reliable location of the interproximal areas. The bumper members, because of their location relative to the spray nozzle, do not interfere with the spray.

The bumper members typically oppose each other and are symmetrical so as to provide a reliable location of an interproximal area. Bristles can also be provided around the exterior of the nozzle to provide additional cleaning capability. This arrangement combines distance (stand-off) protection with interproximal guidance. Also, since it does not in any way block the spray, there is no risk of pooling of the fluid around the landing site for the spray.

FIG. 6 shows a still further embodiment of the guidance tip member for the spray head assembly. This arrangement includes a curved guidance member 86, the curved member including a top portion 88 and two downwardly extending side portions 90 and 92. The opposing longitudinal ends of the curved member are open. The curved member is generally configured so that it fits over and around the teeth 95. The curved member includes at least one spray nozzle 94 which is directed toward the teeth. There may be more than one spray nozzle, including a possible arrangement where the sprays cross each other at a desired angle. In this arrangement, the neck portion of the spray assembly, at the end of which is positioned the guidance member, is flexible, allowing the spray head portion to adapt to the curve of the jaw. The curved member 86 is typically made from flexible material which will allow for variances in the shape and size of the teeth.

Extending downwardly from the interior surface of top portion 88 is a probe member 98, which is arranged to come into contact with the top surface of the teeth (between the teeth for interproximal cleaning), as the curved member is moved along the teeth, providing a safe distance for the spray relative to the gums, etc. This arrangement is convenient in use, in that it is self-guiding along the teeth and flexes as different size/configuration of teeth are encountered. All surfaces of the teeth are cleaned, including upper and side portions as well as interproximal surfaces with this arrangement.

Hence, a guidance tip member has been disclosed which is located at the end of a spray head assembly portion of a droplet spray teeth cleaning system. This arrangement informs the user of the location of the spray relative to the teeth and gums, and reliably positions the spray for interproximal cleaning, as well as the front portions of the teeth. The location of the spray assembly is difficult for the user to ascertain without a guidance member since the location of the spray is often not clearly and precisely recognizable by a sensory feel of the spray.

It should be understood that the guidance member disclosed herein could be used with a hand-held portion of a tethered droplet spray cleaning system as well as a standalone hand held unit, as shown in FIG. 1. Further, the guidance member can be used with various droplet spray teeth cleaning systems/devices, including those which are not gas assisted, i.e. those which do not use gas to produce and accelerate the liquid droplets.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A spray assembly for a droplet spray system for cleaning teeth, comprising:

a spray nozzle and a guidance member positioned at a tip end of the nozzle and configured to direct a spray of liquid, wherein the nozzle is completely recessed within the guidance member, wherein the guidance member is in the form of a sphere configured to fit an interproximal area between two adjacent teeth, wherein the guidance member includes a segmented perimeter formed by a plurality of segments that only partially surround the nozzle and are positioned a selected distance away therefrom, wherein the guidance member includes a primary opening through which the spray from the nozzle is directed and includes at least one or more elongated secondary openings that are separated from the primary opening by a portion of the guidance member to allow fluid to escape therethrough, and which are each larger than the primary opening, and which together with the plurality of segments define the segmented perimeter, and wherein the primary opening of the guidance member is located a distance within a range of 1-15 mm from a nozzle opening of the nozzle.

2. The spray assembly of claim 1, wherein the primary opening of the guidance member is located a distance within a range of 3-8 mm from the nozzle opening.

3. The spray assembly of claim 1, comprising a handle wherein the spray assembly is replaceable relative to the handle.

4. The spray system of claim 3 wherein the handle contains a source of liquid and pressurized gas and a control assembly.

5. The spray system of claim 3 wherein sources of liquid and pressurized gas are contained in a remote unit tethered to the handle.

6. The spray assembly of claim 1, wherein the guidance member is configured so that it does not block liquid spray from the nozzle.

7. The spray assembly of claim 1, wherein the guidance member is configured to allow venting of fluid during operation to prevent pooling of liquid.

8. The spray assembly of claim 1, including a flexible neck portion, at the forward end of which is positioned the guidance member.

9. The spray assembly of claim 1, wherein the primary opening is approximately circular, slightly larger than a spray footprint of the spray nozzle and wherein the one or more secondary openings are in the form of slots.

* * * * *